(12) United States Patent
Jacobs et al.

(10) Patent No.: US 10,297,019 B2
(45) Date of Patent: ***May 21, 2019

(54) REMOTE PHARMACEUTICAL VERIFICATION

(71) Applicant: PerceptiMed, Inc., Mountain View, CA (US)

(72) Inventors: Alan Jacobs, Palo Alto, CA (US); Jennifer Jacobs, Palo Alto, CA (US); Yana Nikitina, San Francisco, CA (US)

(73) Assignee: PERCEPTIMED, INC., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/884,256

(22) Filed: Jan. 30, 2018

(65) Prior Publication Data

US 2018/0225818 A1 Aug. 9, 2018

Related U.S. Application Data

(63) Continuation of application No. 14/905,281, filed as application No. PCT/US2014/050440 on Aug. 8, 2014, now Pat. No. 9,886,751.

(Continued)

(51) Int. Cl.
*G06K 9/00* (2006.01)
*G06T 7/00* (2017.01)
*A61J 7/00* (2006.01)

(52) U.S. Cl.
CPC ........... *G06T 7/0004* (2013.01); *A61J 7/0076* (2013.01); *G06K 9/00* (2013.01); *A61J 2205/00* (2013.01)

(58) Field of Classification Search
CPC ... G06T 7/0004; A61J 7/0076; A61J 2205/00; A61J 7/00; G06K 9/00
See application file for complete search history.

(56) References Cited

U.S. PATENT DOCUMENTS 5,812,410 A * 9/1998 Lion .................... G07F 17/0092
221/9
5,963,136 A * 10/1999 O'Brien ................ A61J 7/0481
340/539.12

(Continued)

FOREIGN PATENT DOCUMENTS

CN 103025301 A 4/2013
JP 2003517335 A 5/2003

(Continued)

OTHER PUBLICATIONS

Chinese First Office Action, Chinese Application No. 201480044292.7, dated Jul. 23, 2018, 16 pages (with concise explanation of relevance).

(Continued)

*Primary Examiner* — Amir Alavi
(74) *Attorney, Agent, or Firm* — Fenwick & West LLP

(57) ABSTRACT

A pill verification system obtains a prescription filled at a pharmacy and gathers information of the pills being dispensed for a remote pharmacist to verify the prescription. As pills are dispensed to a pill vial to fill the prescription, a pill imaging system captures images of the pills, and a pill vial imaging system captures an image of the pill vial. The prescription, pill images, and pill vial image are transmitted to a remote verification system. A pharmacist is presented with the prescription, images of substantially all pills filling the prescription, and the pill vial of the prescription to verify the prescription is correct. The remote verification system may present prescriptions filled from many different pharmacies, permitting increased rate of verification and one pharmacist to support many pharmacies. The pharmacist's verification is transmitted to the pill verification system and displayed for a technician to complete verification of the pills.

20 Claims, 4 Drawing Sheets

Related U.S. Application Data

(60) Provisional application No. 61/864,456, filed on Aug. 9, 2013.

(56) References Cited

U.S. PATENT DOCUMENTS

| | | | | |
|---|---|---|---|---|
| 6,202,923 | B1* | 3/2001 | Boyer | G06F 19/3462 235/375 |
| 8,215,557 | B1* | 7/2012 | Reno | A61J 7/02 235/462.13 |
| 9,886,751 | B2* | 2/2018 | Jacobs | G06T 7/0004 |
| 2003/0086338 | A1* | 5/2003 | Sastry | G06F 19/3462 368/10 |
| 2004/0100415 | A1* | 5/2004 | Veitch | B01L 3/545 343/850 |
| 2005/0168337 | A1* | 8/2005 | Mahoney | G08B 1/08 340/539.12 |
| 2005/0199698 | A1* | 9/2005 | Glynn | G06Q 30/02 235/375 |
| 2006/0124656 | A1* | 6/2006 | Popovich, Jr. | G07F 9/026 221/9 |
| 2008/0059228 | A1* | 3/2008 | Bossi | G06F 19/3418 705/2 |
| 2011/0206238 | A1* | 8/2011 | Kinser | G06K 9/00671 382/103 |
| 2011/0307265 | A1 | 12/2011 | Bannis | |
| 2012/0047049 | A1 | 2/2012 | Cadiz | |
| 2012/0097290 | A1 | 4/2012 | Mikhaeil | |
| 2012/0209627 | A1* | 8/2012 | Moncrief | G06F 19/3418 705/3 |
| 2013/0039564 | A1 | 2/2013 | Eller et al. | |
| 2013/0159712 | A1 | 6/2013 | Sigworth et al. | |
| 2013/0173280 | A1 | 7/2013 | Denny | |
| 2013/0173287 | A1 | 7/2013 | Cashman et al. | |
| 2013/0194414 | A1 | 8/2013 | Poirier et al. | |
| 2015/0261934 | A1 | 9/2015 | Miller | |
| 2016/0163034 | A1 | 6/2016 | Jacobs et al. | |

FOREIGN PATENT DOCUMENTS

| | | |
|---|---|---|
| JP | 2012161510 A | 8/2012 |
| JP | 2013529095 A | 7/2013 |
| WO | WO 00/06078 | 2/2000 |
| WO | WO 2011/112606 | 9/2011 |
| WO | WO 2012/056317 | 5/2012 |
| WO | WO 2013/112591 | 8/2013 |

OTHER PUBLICATIONS

Canadian Office Action, Canadian Application No. 2,920,349, dated Oct. 17, 2016, 6 pages.
Patent Cooperation Treaty, International Search Report and Written Opinion of the International Searching Authority, International Patent Application No. PCT/US2014/050440, dated Nov. 25, 2014, 15 Pages.
U.S. Appl. No. 61/589,750, filed Jan. 23, 2012, Inventors: E. Gershtein et al.
Canadian Office Action, Canadian Application No. 2,920,349, dated Jun. 28, 2017, 3 pages.
European Extended Search Report, European Application No. 14834230.6, dated Jun. 30, 2017, 15 pages.
European Supplementary Search Report, European Application No. 14834230.6, dated Mar. 3, 2017, 7 pages.
Australian First Examination Report, Australian Application No. 2014306320, dated Oct. 30, 2017, 3 pages.
United States Office Action, U.S. Appl. No. 14/905,281, dated Mar. 20, 2017, 12 pages.
Japanese Office Action, Japanese Application No. 2016-533482, dated Feb. 20, 2018, 8 pages.
Australian Second Examination Report, Australian Application No. 2014306320, dated Mar. 23, 2018, 3 pages.
European Examination Report, European Application No. 14834230.6, dated May 9, 2018, 5 pages.

* cited by examiner

REMOTE PHARMACEUTICAL VERIFICATION

CROSS REFERENCE TO RELATED APPLICATIONS

This application is a continuation of U.S. patent application Ser. No. 14/905,281, filed on Jan. 14, 2016, which is a national stage entry of PCT Application Serial No. PCT/US2014/050440, filed Aug. 8, 2014, which claims the benefit of U.S. Provisional Application No. 61/864,456, filed Aug. 9, 2013, each of which is incorporated by reference in its entirety for all purposes, including any appendices and attachments thereof.

BACKGROUND

This invention relates generally to verification of filled pharmaceutical prescriptions, and more specifically to verification of filled pharmaceutical prescriptions remotely from the location where the prescription is filled.

Pharmaceutical prescriptions are ordered by medical practitioners to designate specific pills and other medicines for a patient. The medical practitioner typically writes the prescription, either by hand or electronically, and the prescription is transmitted to the pharmacy. At the pharmacy, the prescription is filled and a pharmacist on-site physically verifies that the prescription written by the medical practitioner matches the pills actually dispensed into a vial or other container. To verify the pills, the pharmacist reviews a label on the vial and reviews the pills actually dispensed into the vial. Any errors, including dispensing a wrong pill or a labeling error, can be dangerous for a patient. However, having a pharmacist on-site at each pharmacy physically reviewing pills is expensive, significantly increasing operating costs for a pharmacy, and often prohibiting a pharmacy from opening in areas that either lack a pharmacist or financially cannot justify opening a pharmacy.

SUMMARY

A pill verification system enables a pharmacist to verify a prescription at a remote location separate from the location where the prescription is filled. The pill verification system receives a prescription from a medical practitioner. The prescription is electronically entered to identify prescription information describing the prescription, such as particular pharmaceutical formulations, dosages, and so forth is termed prescription information. When the prescription is filled in the pharmacy, a pill verification system collects verification information for the pills in the pill vial filled for that prescription. The verification information is information sufficient to uniquely identify a pill, for example images of pills filling the vial, a machine verification of the pills, spectrometer data, pill weight, and so forth. The verification information may include one or more images of each pill in the pill vial, one or more images of groups of pills in the pill vial, or a pill verification from a pill verification system that verified each pill in the pill vial is consistent with the prescription information. Images of an individual pill may include images of the pill from multiple views, or may include an image of a circumferential view of the pill. In addition, label information including an image of the label of the filled pill vial or a label verification from a label verification system, is captured. In one embodiment, the label information is information for a label to be printed and affixed to the pill vial rather than a label already affixed to the pill vial. The pill verification system transmits this information (prescription information, verification information, and label information) to a pharmacist at a remote verification system for final review and approval.

The remote verification system displays this information to the pharmacist. The pharmacist reviews the prescription, the verification information, and the label information to verify the prescription has been properly filled. The pharmacist in one embodiment is provided the label image and images of each pill that filled the prescription. The pharmacist's verification is logged by the remote verification system and returned to the pill verification system where the prescription is filled. The pill verification system displays the verification result from the pharmacist and provides the result to a pharmacy technician. The pill verification system in one embodiment securely holds the pill vial until a verification result has been received. The pharmacy technician at the pharmacy may then place the verified filled prescription in a holding area or may dispense the prescription to the patient.

In one embodiment, the pill verification system incorporates a pill imaging system that captures images of pills filling a pill vial, along with a pill vial imaging system. In this embodiment, the pill verification system captures images of the pills filling the vial along with the image of the pill vial itself, and may perform related verification of the pills or the pill vial. The pill verification system in this embodiment provides the prescription, pill verification information, and label information to the remote verification system and displays a verification result received from the remote verification system.

The figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION

Overview

Figure 1:
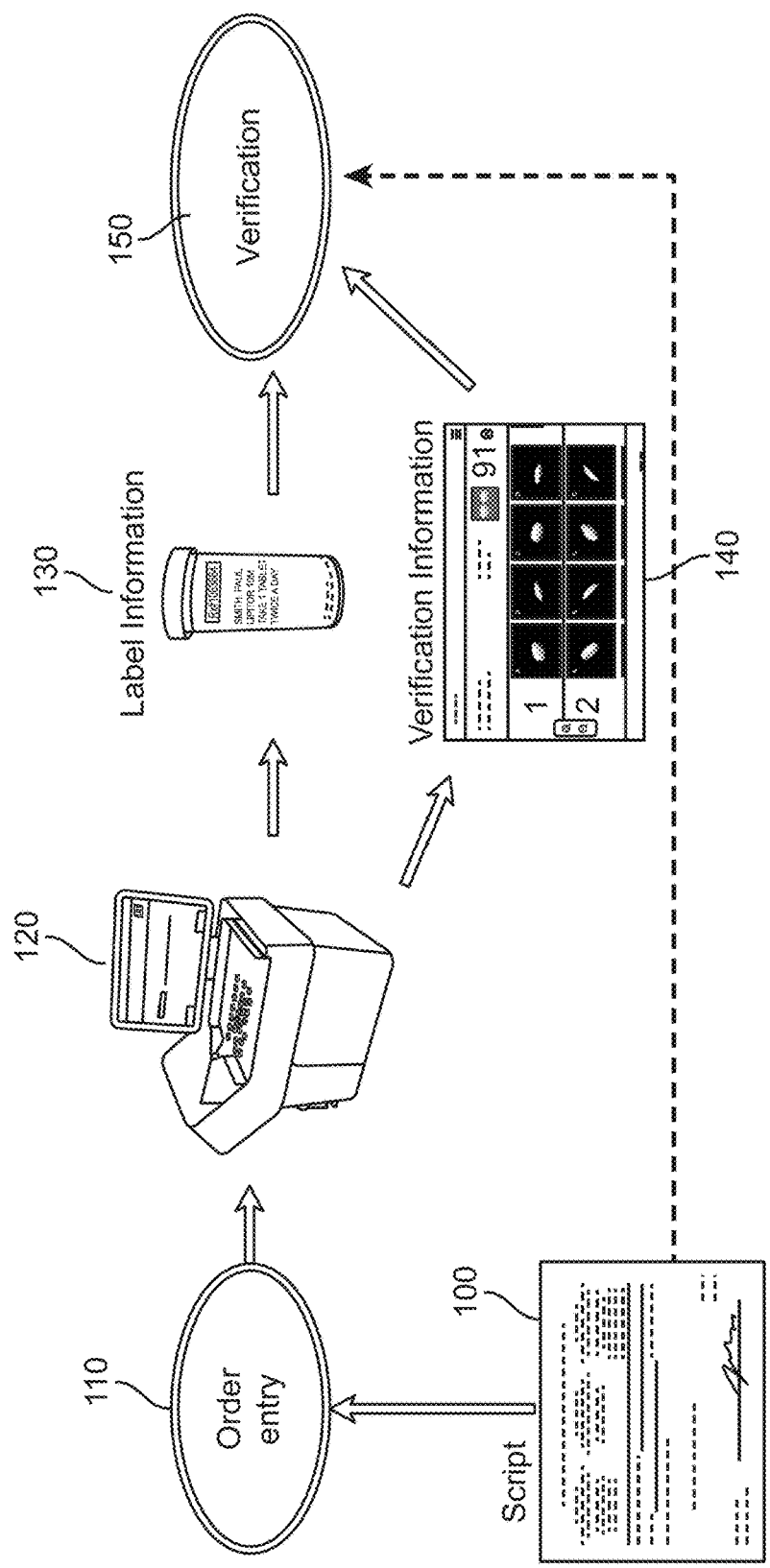
FIG. 1 illustrates a workflow using systems and methods for verification of pills according to one embodiment.

FIG. 1 illustrates a workflow using systems and methods for verification of pills according to one embodiment. Initially, a pharmacy receives a prescription 100 from a medical practitioner, such as a doctor or nurse practitioner. The prescription 100 may be a written prescription provided by a patient, or the pharmacy may receive the prescription 100 directly from the medical practitioner electronically, by fax, by telephone or otherwise. The prescription 100 specifies various information about a medication to be dispensed to the patient. Depending on the particular prescription 100, the prescription may specify a quantity, a specific pharmaceutical composition (i.e., one or more specific drugs and/or dosages thereof, a specific manufacturer), instructions for the patient to use the prescription, and other details.

The prescription is brought to or provided electronically to a pharmacy, where the order is entered 110. The order may be entered electronically by a medical practitioner contacting a pharmacy directly or a pharmacy technician at the pharmacy may enter the order 110. The order is entered into a pharmaceutical tracking system (not shown) at the pharmacy. Some systems may themselves auto-generate an order based on electronic prescription information received. The pharmaceutical tracking system may also capture an image of the prescription if the prescription was hand-written. The electronically captured information about the prescription is termed prescription information, which may include the specific quantity, composition, instructions, and so forth for the prescription, and may include an image of the written prescription itself. The pharmaceutical tracking system stores patient and prescription information and maintains records of prescriptions filled at the pharmacy. When the pharmacy fills the prescription, a pharmacy technician selects a vial for dispensing the prescription, prints a label for the vial, attaches the label to the vial, and obtains the desired pills for the prescription from a stock.

Prior to filling the prescription and providing a pill vial with pharmaceuticals to the patient, the pharmacy technician loads the pills into a pill verification system 120. The pill can be any type or shape, including tablets, capsules, etc. The pill verification system 120 in one embodiment receives the pills and obtains images of each pill. One example of a pill verification system is described in Patent Cooperation Treaty Pub. No. WO/2011/112606, which is hereby incorporated by reference in its entirety. In one embodiment of a pill verification system, pills travel down a chute and images are captured of each pill as it is moving down the chute by cameras (e.g., four cameras in one example) at different angles (typically orthogonal to one another) to the pill. This captures images of the pill from multiple angles and allows a view of many aspects of the pill for verification purposes. In one embodiment of the pill verification system 120, the pill vial is located at the end of the chute and collects the pills after the images are captured. In this embodiment, the pill verification system 120 produces verification information 140 including the images of each pill. The verification information 140 includes information representing each pill or substantially each of the pills to be added into the vial, and is used by a pharmacist to determine whether the pill vial is filled with the appropriate type of pill.

In one embodiment of the pill verification system 120, the pill verification system 120 also performs an analysis of the pills to determine the pill type. In this embodiment, the pill verification system 120 also receives the prescription information to determine whether the pill type matches the pharmaceutical composition stated on the prescription. The pill verification system 120 may retrieve the prescription information from the pharmaceutical tracking system, or may read a barcode printed on the pill bottle label, or obtain the desired pill type another way.

Using the desired pill type determined from the prescription information, the pill verification system 120 in this embodiment performs an automated verification of the pills. Pill verification methods are described in U.S. Patent App. No. 61/589,750, filed Jan. 23, 2012, and Patent Cooperation Treaty App. PCT/US2013/022754, each of which is hereby incorporated by reference in its entirety. To determine a pill type, the pill verification system 120 analyzes each image of the pill to determine a feature vector including features describing the pill, such as color, shape, imprints on the pill, and other aspects of the pill. The pill verification system 120 processes the feature vectors using at least one classifier trained on a database of pill images and associated pill types. As a result of the classification, the pill verification system 120 determines a pill type for the pill and whether the pill type matches the prescription information, including whether it is the correct type of pill and whether it is the correct dosage as stated in the prescription information. Thus, the verification information 140 may include a pill verification indicating whether the pill verification system 120 identified the pill images as consistent with the prescription information. In one embodiment, the pill verification system 120 provides verification information 140 that includes a group of images (e.g., four images) for each pill, along with a determination of a pill type and whether the pill type matches the prescription. The verification information 140 may also include a quantity of pills in the pill vial.

In another embodiment, the pill verification system 120 provides the pill verification determined by the pill verification system 120 as the verification information, which may not include any pill images. In this embodiment, the pill verification system 120 may verify the type of pill using pill images as described above, or may verify the pill type using another suitable technique.

In addition to the verification information 140, the pill verification system 120 in one embodiment also receives label information 130 identifying the labeling on the pill vial. To identify the label on the pill vial, the pill vial and the label on the pill vial are also captured as an image in one embodiment. A pill vial imaging system captures an image of the pill vial with the label applied to the pill vial. In other embodiments, the label may be captured separately from the pill vial, or the pill vial label may be automatically generated based on the prescription information. The pill vial image is captured in one embodiment to generate a circular "landscape" view of the pill vial, such that the entire exterior of the pill vial may be viewed. In one embodiment, the landscape view is captured by multiple cameras placed around the pill vial. In this embodiment, the pill vial imaging system combines the images from the multiple cameras into a single landscape image. In one embodiment, rather than the pill vial image, the label information is a label to be printed and affixed to the pill vial.

In one embodiment, the pill vial imaging system provides a label verification from a label verification system. The label verification system may determine the verification of the label using, e.g., character recognition of textual characters on the pill, and analyze the characters to verify that the label on the vial matches the prescription. The label verification may be included with the label information 130. It may be preferred to capture the pill vial image of the actual pill vial, so that after verification of the pills, the pills may simply be added to the appropriate (already verified) vial and sealed. In another embodiment, the pill vial is labeled and filled with the pills that were imaged by the pill verification system 120. In this embodiment, after verification of the pills and the pill vial, the pill vial can be immediately sealed after verification by the remote pharmacist, either by a pharmacist technician or by an automated mechanism.

To verify the contents of the pill vial and determine that the prescription 100 ordered by the medical practitioner is appropriately filled, one or more of the prescription 100, the pill verification information 140, and the label information 130 are transmitted to a remote verification system 150 for a pharmacist to review. The pill verification system 120 manages this workflow and process in one embodiment.

Figure 3:
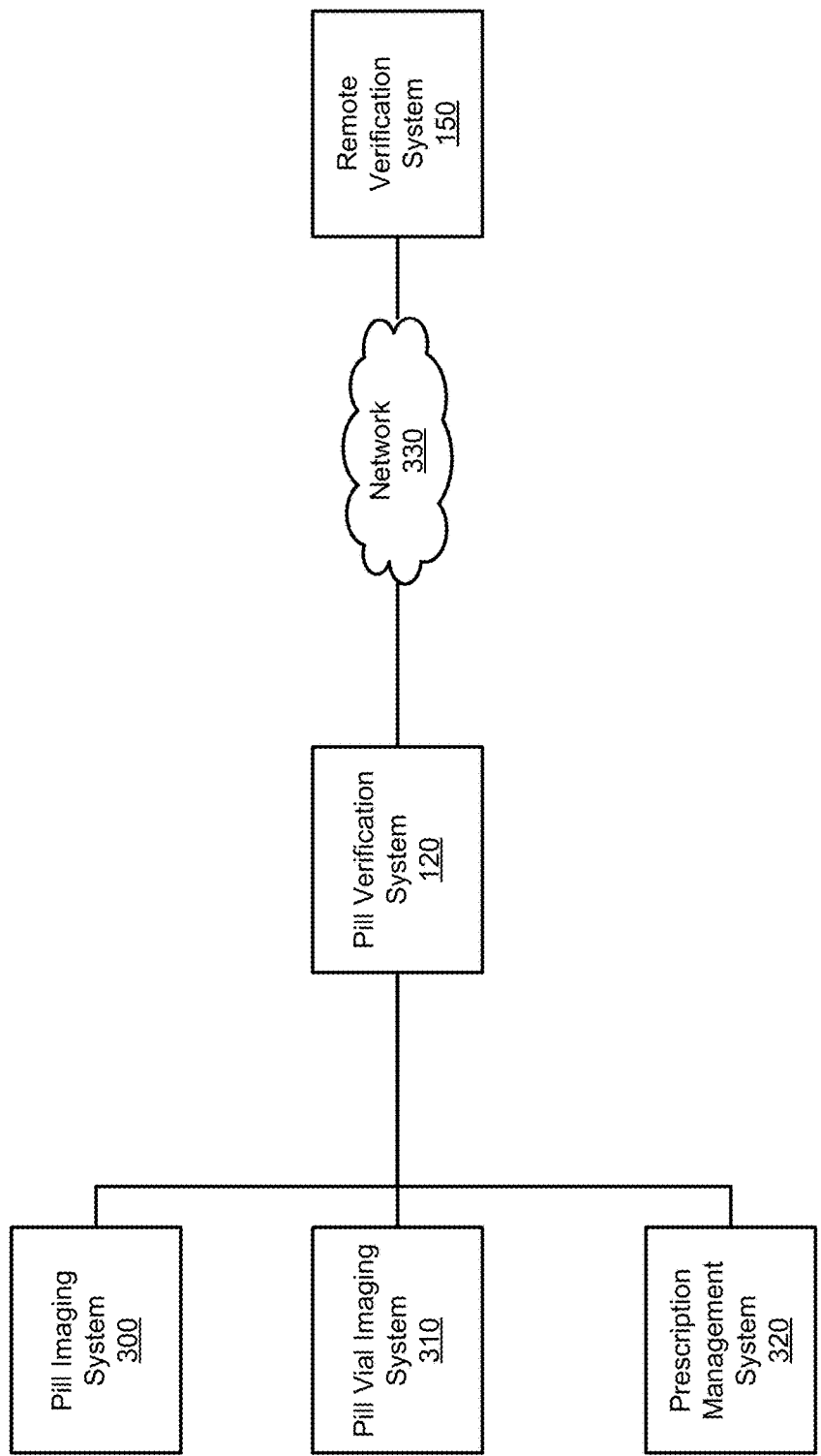
FIG. 3 shows an embodiment of a pill verification system separate from the pill imaging and pill vial imaging systems.

FIG. 3 shows an embodiment of a pill verification system 120 separate from the pill imaging and pill vial imaging systems. The pill verification system 120 shown in this embodiment is a separate computing system from the pill imaging system and is a computer system which receives and processes pill verification information. The verification system 120 receives the prescription information, pill verification information 140 and label information 130 and transmits this package to the remote verification system 150 to display for pharmacist review. A pill imaging system 300 captures images of pills to provide pill verification information 140 to pill verification system 120. The pill images captured by pill imaging system 300 may include several images of individual pills to be added to a pill vial, as described above, and may also perform pill verification of the pills. This verification information 140 is transmitted from the pill imaging system 300 to the pill verification system 120. Similarly, the pill vial imaging system 310 obtains label information by capturing an image of the pill vial or otherwise identifying information about the label to be added to the pill vial for the prescription. The pill verification system 120 also receives the prescription information from prescription management system 320, which may include an image of the prescription 100.

Pill verification system 120 transmits the information used for pill verification by a pharmacist via a network 330 to remote verification system 150. Such information in one embodiment include the prescription, verification information associated with the pills (e.g., pill images), and label information (e.g., a label image). The remote verification system 150 displays the information to a remote pharmacist, who accepts or rejects the filled prescription.

The remote verification system 150 displays information for a pharmacist to verify a filled prescription. The remote verification system 150 is a computing system that includes a display and is configured to receive pill information, display the information, and transmit verification results input by a pharmacist to the pill verification system 120 at the pharmacy. The remote verification system 150 may be a display controlled remotely by the pill verification system 120, or may include a separate computing system with a processor and other computing components for receiving pill information and displaying it to a pharmacist. The remote verification system 150 receives the information transmitted by the pill verification system 120 and manages the presentation of that information to a pharmacist for verification. The remote verification system and display of information to the pharmacist is further described with respect to FIG. 2.

Figure 4:
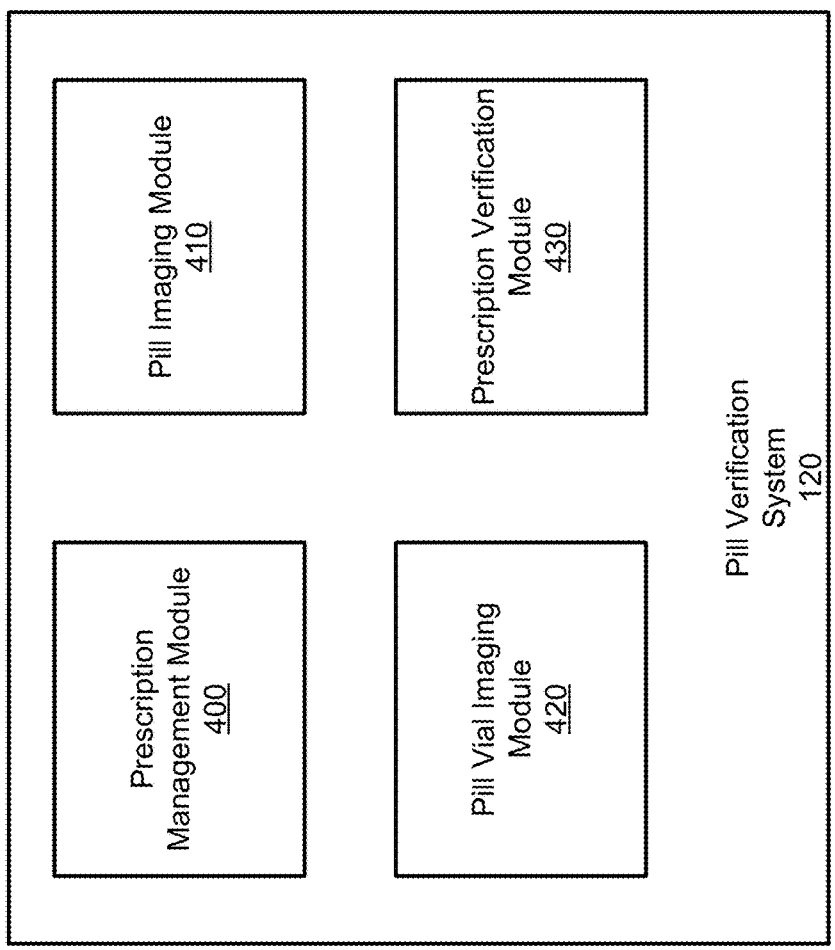
FIG. 4 shows components of a verification system according to one embodiment.

FIG. 4 shows components of a verification system 120 according to one embodiment. In this embodiment, the verification system 120 includes a prescription management module 400 that receives prescription information from the prescription management system 320, a pill vial imaging module 420 that receives pill vial information from the pill vial imaging system 310, and a pill imaging module 410 that receives pill verification information from pill imaging system 300. A prescription verification module 430 collects the data received from each of these modules and transmits the information to the remote verification system 150 for display to the pharmacist for verification. The prescription verification module 430 receives a verification result from the remote verification system 150 and displays the verification result to an operator of the pill verification system 120.

In one embodiment, the pill imaging system 300 is incorporated into the pill verification system 120. In additional embodiments, the pill verification system 120 maintains the pill vial during the verification process, such that the pill verification system 120 displays the results of the verification to the pharmacy technician or other user who is filling the prescription prior to removal of the pill vial from the pill verification system 120.

In one embodiment, the pill verification system 120, pill vial imaging system 310, and pill imaging system 300 are incorporated into a single unit. In one example of this embodiment, the pill verification system 120 receives the pill vial in a pill vial holder and separately receives the pills to fill the prescription. The pills are passed through a pill imager, which captures images of the pills, and added to the pill vial. The pill vial imaging system captures images of the pill vial before, during, or after the pill vial is filled with the pills exiting the pill imager. The pill verification information is transmitted to a display for pharmacist review while the pill vial is held in the pill vial holder. In this embodiment, the pill vial holder may be configured to retain the pill vial until the verification is received from the remote pharmaceutical system.

Figure 2:
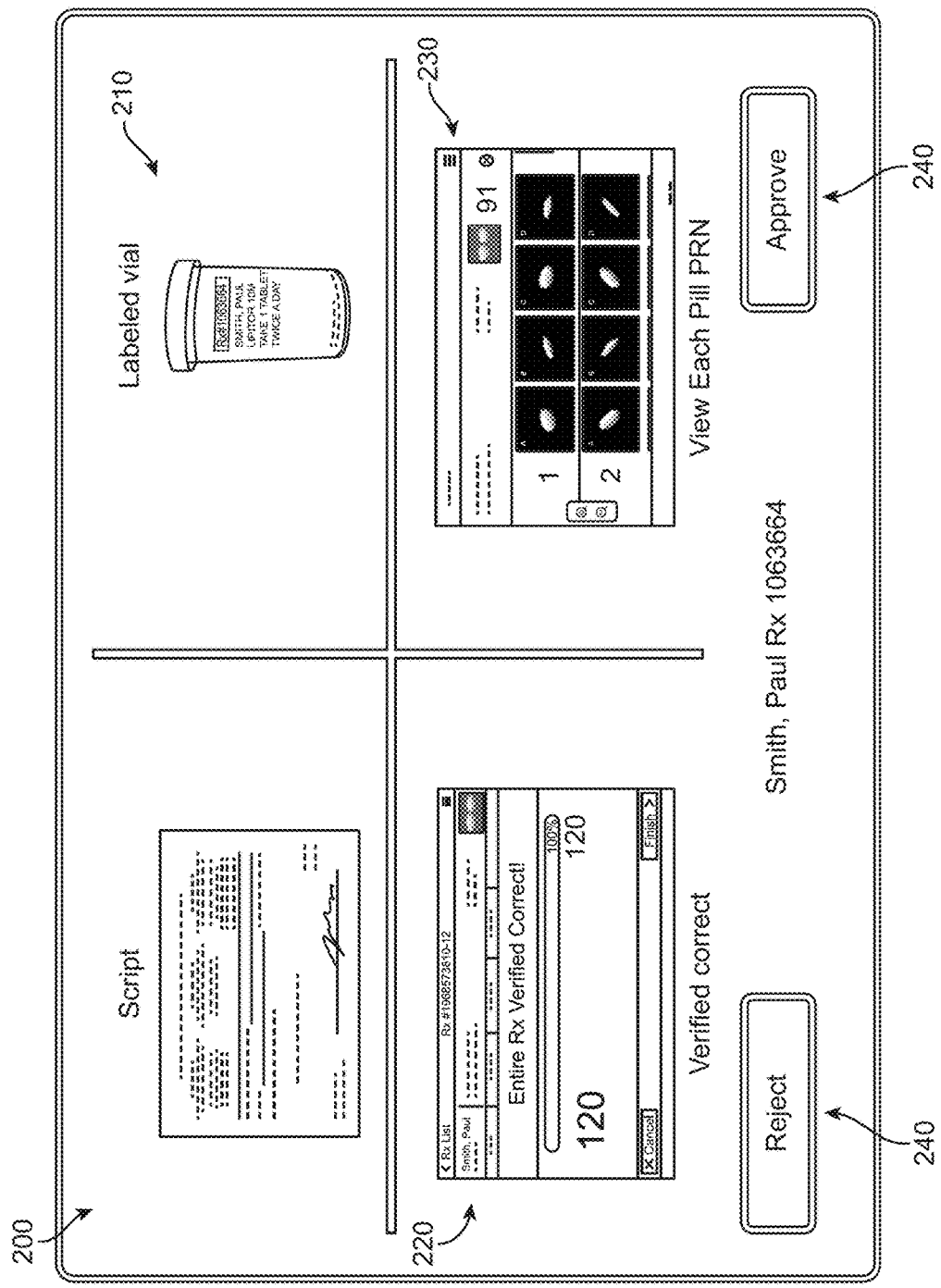
FIG. 2 shows a display for pharmacist review of the filled prescription order according to one embodiment.

FIG. 2 shows a display for pharmacist review of the filled prescription order according to one embodiment. The display for pharmacist review is located remotely to a location where the pills are selected for the pill vial and where the vial is labeled (e.g., the pharmacy). The display includes sufficient information for the pharmacist to verify that the prescription does not include errors without requiring the pharmacist to personally oversee the filled prescription and as a result. This does not require the personal time of a pharmacist to review prescriptions, and permits greater throughput from a pharmacy. In addition, the display may include a queue of prescriptions to be verified by the pharmacist, which may be prescriptions from many different pharmacies and pill verification systems 120.

In other embodiments, the display for pharmacist review is located near the location where the pills are selected and the vial is labeled. For example, the remote verification system may also be implemented in any situation where the pharmacist does not personally oversee the filled prescription, including a pharmacist verifying the prescription from a separate counter or room at a pharmacy.

As shown in the user interface displayed in FIG. 2, the interface for pharmacist review may include several panels displaying information about the filled prescription. The particular layout shown in FIG. 2 is an example, and other configurations may also be used. In addition, the display may not include all of the components illustrated in FIG. 2, or additional components based on the information provided by the pill verification system 120. The pharmacist is presented with the prescription 200, which may include an image of a hand-written prescription, or an electronic prescription, such as entered at a prescription management system 320. The pharmacist may review the prescription 200 to verify that the verification information about the pills and the label information is correct. The display also includes a pill vial image 210. The pill vial image 210 displays the label information indicating the instructions and contents of the pill vial as described by the label on the pill vial. This permits the pharmacist to verify the prescription has accurately been transcribed from the prescription 200 to the pill vial and that the instructions for the customer (as printed on the vial) are correct.

In the embodiment shown in FIG. 2, the pill verification information includes a pill verification indication 220 that the pill verification system 120 matched the pill type of the pills to the desired pills of the prescription. In this embodiment, the verification information includes pill images from the pill imaging process and a pill verification from automated analysis of the pill images. A pill image gallery 230 is also shown to the pharmacist. The pharmacist may review the gallery of pill images to verify that individual pills imaged by the pill verification system 120 match the characteristics in size, color, shape, imprint, and other features of the pharmaceutical composition that was prescribed (or in the case of a replacement generic, of the replacement generic). In some embodiments, the pharmacist has access to images of all of the pills or substantially all of the pills in the vial. In other embodiments, the pharmacist has access to images of at least 50%, 60%, 70%, 80%, 90%, 95%, 99% or other percentages of the pills in the vial. When there are any errors in the pill type identified by the pill verification system 120 (i.e., the identified pill type does not match the expected pill type), any pill that did not match may be highlighted in the gallery 230 for quick identification and review by the pharmacist. After reviewing the pill verification information, the pharmacist provides a verification result on an interface 240 whether the prescription is properly filled. In one embodiment, such as when the pill verification information does not include pill images, the display provides the pill verification indication 220 without the corresponding pill image gallery 230.

Using this method, the pharmacist is presented with sufficient information to quickly and easily verify the proper filling of a prescription. The pill verification information enables the pharmacist to review information relating to each of the pills added to the pill vial. When the pill type matching is available, the pharmacist gains comfort that the pill has been verified by the pill verification system, and when pill images are available, the pills can be quickly reviewed by the pharmacist using the images of the pill in the gallery 230, in particular any errors identified by the pill verification system 120. With this system and corresponding workflow, a pharmacist at a central location can review and verify pills from a large number of satellite pharmacies while maintaining high confidence of faithfully dispensing prescriptions. In addition, a pill verification system that incorporates a pill imaging and verification system can incorporate the pharmacist's verification in its displayed results, providing additional confidence in the displayed verification results.

In alternate embodiment of the remote pill verification, rather than a pharmacist performing the remote verification, the pills are automatically verified by another system remote from the location where prescriptions are filled. Thus, the data received from a local pharmacy may be presented via an interface to a pharmaceutical validation system rather than a human pharmacist. The interface in one example is an application programming interface (API) to another application located at the remote pharmacist system. The pharmaceutical validation system determines whether the provided prescription information, validation information, and label information is acceptable and this response is transmitted back to the local pharmacy.

Summary

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described.

Embodiments of the invention may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments of the invention may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

What is claimed is:

1. A method for remote verification of a filled prescription, the method comprising:
   receiving pill verification information from a pill verification system of at least one pill filling a prescription, the pill verification information comprising at least one image of the at least one pill filling the prescription;
   displaying the pill verification information on a display, wherein the display enables a user to review the pill verification information including at least one image of the at least one pill filling the prescription;
   receiving a response to the pill verification information from an interface, the response accepting or rejecting the filled prescription; and
   transmitting the response to a prescription filling location.

2. The method of claim 1, wherein the pill verification information further comprises at least one of the following: an indication from the pill verification system regarding whether one or more pills of the filled prescription matches a pharmaceutical composition of the prescription, a quantity of pills in the filled prescription, and verification information of substantially all of the at least one pill filling the prescription.

3. The method of claim 1, wherein displaying the pill verification information on the display comprises displaying a gallery of images, wherein each image corresponds to at least one pill of a plurality of pills of the filled prescription.

4. The method of claim 3, wherein each image includes corresponding verification information, wherein the display is configured to highlight an image in the gallery when the verification information indicates a mismatch between the pill in the image and a pharmaceutical composition of the prescription.

5. The method of claim 1, further comprising:
receiving prescription information for the prescription to be dispensed to a patient; and
displaying the prescription information on the display.

6. The method of claim 5, wherein the prescription information comprises one or more of the following: a pharmaceutical prescription written by a medical practitioner, a quantity of pills in the filled prescription, a pharmaceutical composition of the at least one pill, a dosage of the at least one pill, a manufacturer of the at least one pill, and patient instructions for administering the filled prescription.

7. The method of claim 1, further comprising:
receiving pill vial information comprising one or more of the following: an image of a pill vial depicting a label on the pill vial, a verification of the label on the pill vial from a label verification system, and a label to be printed for the pill vial; and
displaying the pill vial information on the display.

8. The method of claim 7, wherein the image of the pill vial comprises a landscape view of the pill vial.

9. The method of claim 1, wherein the at least one image comprises a circumferential view of the at least one pill.

10. The method of claim 1, wherein the pill verification information comprises a plurality of images including several views of the at least one pill.

11. The method of claim 1, wherein the display includes a queue of a plurality of filled prescriptions to be verified.

12. The method of claim 11, wherein the plurality of prescriptions are filled at different pharmacies.

13. The method of claim 1, further comprising:
retaining a pill vial containing the filled prescription; and
releasing the pill vial in response to receiving a response accepting the filled prescription.

14. A non-transitory computer-readable medium comprising instructions that when executed by a processor cause the processor to perform steps of:
receiving pill verification information from a pill verification system of at least one pill filling a prescription, the pill verification information comprising at least one image of the at least one pill filling the prescription;
displaying the pill verification information on a display, wherein the display enables a user to review the pill verification information including at least one image of the at least one pill filling the prescription;
receiving a response to the pill verification information from an interface, the response accepting or rejecting the filled prescription; and
transmitting the response to a prescription filling location.

15. The computer-readable medium of claim 14, wherein displaying the pill verification information on the display comprises displaying a gallery of images, wherein each image corresponds to at least one pill of a plurality of pills of the filled prescription.

16. The computer-readable medium of claim 14, wherein each image includes corresponding verification information, wherein the display is configured to highlight an image in the gallery when the verification information indicates a mismatch between the pill in the image and a pharmaceutical composition of the prescription.

17. The method of claim 14, wherein the pill verification information comprises a plurality of images including several views of the at least one pill.

18. The method of claim 14, wherein the display includes a queue of a plurality of filled prescriptions to be verified.

19. The method of claim 18, wherein the plurality of prescriptions are filled at different pharmacies.

20. The method of claim 14, wherein the instructions further cause the processor to perform the steps of:
retaining a pill vial containing the filled prescription; and
releasing the pill vial in response to receiving a response accepting the filled prescription.

* * * * *